United States Patent [19]

Cabrera Garrido et al.

[11] Patent Number: 5,676,962
[45] Date of Patent: Oct. 14, 1997

[54] INJECTABLE MICROFOAM CONTAINING A SCLEROSING AGENT

[76] Inventors: Juan Cabrera Garrido; Juan Cabrera Garcia-Olmedo, both of Porton De Tejeiro, 2, Granada, Spain, 18005

[21] Appl. No.: 407,595

[22] Filed: Feb. 23, 1995

Related U.S. Application Data

[63] Continuation of PCT/ES94/00064 Jun. 21, 1994.

[30] Foreign Application Priority Data

Jun. 23, 1993 [ES] Spain ................................. 9301413

[51] Int. Cl.$^6$ ........................................... A61F 2/01
[52] U.S. Cl. ..................... 424/423; 424/489; 424/484; 424/DIG. 7; 514/706; 514/708; 514/709; 514/945
[58] Field of Search ............................ 514/945, 706, 514/708, 709; 424/400, 423, 489, DIG. 7, 484

[56] References Cited

U.S. PATENT DOCUMENTS 4,466,442   8/1984   Hilmann et al. ..................... 128/653

FOREIGN PATENT DOCUMENTS 324 938     7/1989   European Pat. Off. .
WO 92/05806  4/1992   WIPO .

*Primary Examiner*—James J. Seidleck
*Assistant Examiner*—Michael A. Williamson
*Attorney, Agent, or Firm*—Darby & Darby

[57] ABSTRACT

Injectable microfoam for scleroteraphy. The sclerotherapy of varices is based on the injection of liquid substances capable of suppressing them. The present invention relates to the preparation of sclerosing substances in the form of a microfoam. The microfoam is prepared with sclerosing agents, and is then injected in the vein to be treated, so that the microfoam displaces the blood contained in the vein and provides for the contact of the sclerosing agent with the vascular endothelium, with a predetermined known concentration and during a controllable time.

20 Claims, No Drawings

INJECTABLE MICROFOAM CONTAINING A SCLEROSING AGENT

This is a continuation of international application Serial No. PCT/ES94/00064, filed Jun. 21, 1994.

PRIOR ART

Schlerosis of varices is based on injecting liquid substances in them, which causing a localized inflammatory reaction propitiates the elimination of these abnormal veins.

Upon injecting a sclerosing agent, a mixture thereof with the blood contained in the vein is produced and diluted in an unknown proportion. The results are uncertain (due to overdose or underdose) and limited to short varicose segments. As the size of the varices to be injected decreases, the lesser this dilution is and the results that are obtained are more foreseeable. Nowadays, sclerosis is a technique chosen in cases of small and medium-sized varices. Surgery is used for those varices with a diameter equal or larger than 7 mm.

Sclerosis and surgery complement each other at this time, but sclerotherapy continues without being able to be applied to large varicose trunci.

In these large sized varices, upon injecting a sclerosing substance, the concentration thereof in the vein, its homogenous distribution in the blood and the time that it is going to be in contact with the inside walls of the treted vein are unknown.

In 1946 Orbach injected in small caliber varices some few cubic centimeters of air and verified displacement of the blood inside the vessel, which is occupied by the injected air. The sclerosing agent introduced afterwards is more effective than if it has been injected into the blood.

In thick varices, upon injecting air, the described phenomenon of displacement of the blood by the injected air does not take place, but rather this forms a bubble inside the vein that makes the process ineffective in these vessels.

This same author conceived, a few years late, injection of foam obtained by agitating in a container containing sodium tetradecyl sulfate, an anionic sclerosing detergent with a high foaming capacity.

The process turns out to be rather useless due to the large-sized bubbles formed and dangerous due to the collateral effects of the atmospheric nitrogen, not very soluble in blood.

Both methods had very little practical repercussion as they were used only in small varices.

DESCRIPTION OF THE INVENTION

This invention refers to the preparation of a sclerosing microfoam.

In accordance with the present invention it has been discovered that injecting in a horizontal position a microfoam of pharmacologically inert sterile physiological serum, it is verified that the microfoam causes displacement of the blood contained in the vessel, even in more developed varices, due to the fact that the pressure of the blood contained in them horizontally is low.

The lifting of the injected member decreases even more the venous pressure, facilitating the exclusive filling of the vein with microfoam; this remaining in the vessel while the patient is not lifted from the examination table.

Upon replacing the prepared microfoam with the physiological serum by microfoam prepared with a sclerosing agent and injecting it in the vein, this displaces the blood that the vein contains and guarantees the contact of the sclerosis agent with the endothelium of the vein, at a known concentration and for a controllable amount of time, achieving sclerosis of the entire occupied segment.

The advantages of this process allow:

1. To know the concentration of the sclerosing agent in the vessel, as the microfoam displaces the blood and is not diluted in it like a liquid in it.

2. To guarantee the homogenous distribution of the product of sclerosis in the inside thereof.

3. To control the time in which it is kept in contact with the inside walls of the vein.

All of these factors are not known exactly nor are they controllable with the use of liquid sclerosing agents.

The elaboration of the present invention is carried out with the preparation of a microfoam with any sclerosing agent, such as: polydocanol, sodium tetradecly sulfate, hypertonic glucosated or glucosaline solutions, chromated glycerol, ethanolamine oleate, sodium morrhuate, iodated solutions.

Once the sclerosing microfoam has been prepared by any one of the existing processes, two of which will be described hereinafter, it is introduced in any sterile vessel that can be used later to be injected in the vessels to be treated, and that permits the stability of the same, so that it can be removed by a syringe, or by any other instrument that allows injection thereof into the vessels to be treated.

EXAMPLE 1

The preparation of the sclerosing microfoam is done by mixing in a sterile, hermetic container and connected if desired to a bottle under oxygen pressure, mixture of oxygen and carbon or other physiological gasses; mechanical beating is carried out by means of a micromotor that makes an écouvillon submerged in the sclerosing solution to be foamed turn.

Beating between 8,000 and 15,000 rpm, for a time between 60 and 120 seconds, the microfoam is achieved.

This is introduced into any container that can be used for subsequent storage and later injection into the veins to be sclerosed.

In the event that the sclerosing agent does not have a foaming capacity Polysorbate 20, Polysorbate 80, Polygeline or any other substance with a foaming capacity accepted as inert for intravenous use is added to it.

EXAMPLE 2

The sclerosing agent is introduced into a hermetic, pressurized and sterile container and by stirring the solution the microfoam is achieved, with a outlet from the container for its subsequent use.

What is claimed:

1. Prepared or extemporaneously prepared injectable microfoam for therapeutic uses characterized in that the microfoam is prepared with any sclerosing substance.

2. Injectable microfoam for therapeutic uses, according to claim 1, characterized in that the sclerosing substance is polydocanol.

3. Injectable microfoam for therapeutic uses, according to claim 1, characterized in that the sclerosing substance is sodium tetradecyl sulfate.

4. Injectable microfoam for therapeutic uses, according to claim 1, characterized in that the sclerosing substance is a hypertonic glucostated or glucosaline solution.

5. Injectable microfoam for therapeutic uses, according to claim 1, characterized in that the sclerosing substance used is chromated glycerol.

6. Injectable microfoam for therapeutic uses, according to claim 1, characterized in that the sclerosing substance used is ethanolamine oleate.

7. Injectable microfoam for therapeutic uses, according to claim 1, characterized in that the sclerosing substance used is sodium morrhuate.

8. Injectable microfoam for therapeutic uses, according to claim 1, characterized in that the sclerosing substance used is any iodated solution.

9. A method for phlebologic treatment comprising injecting the microfoam of claim 1 into vessels to be treated.

10. A method for phlebologic treatment comprising injecting the microfoam of claim 2 into vessels to be treated.

11. A method for phlebologic treatment comprising injecting the microfoam of claim 3 into vessels to be treated.

12. A method for treatment of esophageal varices comprising injecting the microfoam of claim 1 into vessels to be treated.

13. A method for treatment of esophageal varices comprising injecting the microfoam of claim 2 into vessels to be treated.

14. A method for treatment of esophageal varices comprising injecting the microfoam of claim 3 into vessels to be treated.

15. A method for proctologic treatment comprising injecting the microfoam of claim 1 into vessels to be treated.

16. A method for proctologic treatment comprising injecting the microfoam of claim 2 into vessels to be treated.

17. A method for proctologic treatment comprising injecting the microfoam of claim 3 into vessels to be treated.

18. A method for angiologic treatment comprising injecting the microfoam of claim 1 into vessels to be treated.

19. A method for angiologic treatment comprising injecting the microfoam of claim 2 into vessels to be treated.

20. A method for angiologic treatment comprising injecting the microfoam of claim 3 into vessels to be treated.

* * * * *